United States Patent [19]

Demopoulos et al.

[11] Patent Number: 5,204,114
[45] Date of Patent: Apr. 20, 1993

[54] METHODS OF MANUFACTURING HIGH DOSAGE GLUTATHIONE THE TABLETS AND CAPSULES PRODUCED THEREBY

[75] Inventors: Harry B. Demopoulos, Scarsdale; Joel Ross, Ardsley, both of N.Y.

[73] Assignee: Health Maintenance Programs, Inc., Elmsford, N.Y.

[21] Appl. No.: 859,892

[22] Filed: Mar. 30, 1992

[51] Int. Cl.$^5$ .......................... A61K 9/20; A61K 9/48
[52] U.S. Cl. ................... 424/465; 424/451; 424/464; 514/474; 514/960; 514/970
[58] Field of Search ............ 424/451, 464, 465; 514/970, 960, 474

[56] References Cited

U.S. PATENT DOCUMENTS

| | | | |
|---|---|---|---|
| 3,873,713 | 3/1975 | Haas et al. | 514/474 |
| 4,203,997 | 5/1980 | Küppers et al. | 514/960 |
| 4,454,125 | 6/1984 | Demopoulos | 514/52 |
| 4,777,033 | 10/1988 | Ikura et al. | 424/487 |
| 5,120,762 | 6/1992 | Hanaoka et al. | 514/970 |

Primary Examiner—Thurman K. Page
Assistant Examiner—Amy Hulina
Attorney, Agent, or Firm—Lerner, David, Littenberg, Krumholz & Mentlik

[57] ABSTRACT

The present invention relates to methods of neutralizing or dissipating the electrostatic charge of glutathione so as to render it susceptible to be included in high glutathione content solid dosage forms. Capsules and tablets including high levels of glutathione are also described.

20 Claims, No Drawings

METHODS OF MANUFACTURING HIGH DOSAGE GLUTATHIONE THE TABLETS AND CAPSULES PRODUCED THEREBY

FIELD OF THE INVENTION

The present invention relates to methods of forming tablets or capsules from glutathione and the tablets and capsules produced thereby.

BACKGROUND OF THE INVENTION

Most recently, glutathione has come under increasing attention as a therapeutic agent. Glutathione has been suggested for the treatment of chemical toxicities, especially the toxicities associated with heavy metal poisoning and cancer chemotherapeutic regimes. See BE no. 904717 and ZA no. 8707502J. See also L. Domingo, et al., *Toxicology* vol. 62 pp. 203-211, 1990; Di Re, et al., *Cancer Chemotherapy and Pharmacology*, vol. 25, pp. 355-360, 1990; L. Cozzaglio et al., *Tumori*, vol. 76 pp. 590-594; M. T. Nobile et al., *Tumori*, vol. 75 pp. 257-258, 1989. Glutathione, in its reduced form, is known to be critical for optimal immune system function. Furukawa et al., *Mechanisms of Aging and Development*, vol. 38 pp. 107-117, 1987; Droge et al., *Immunobiology*, vol. 172 pp. 151-156, 1986; Suthanthiran, et al., *Proceedings of the National Academy of Sciences*, vol. 87 pp. 3343-3347, 1990.

Glutathione may be administered by a number of conventional techniques such as interperitoneally, by aerosol to the lungs, or intravenously. However, aerosol administration ha been shown not to raise the effective levels of glutathione in plasma. The other forms of administration mentioned above are painful, inconvenient, and not necessarily effective in providing long term, meaningful levels of glutathione in plasma. See Aebi et al., *European Journal of Clinical Investigation*, vol. 21, pp. 103-110, 1991.

Not surprisingly, oral dosage forms are preferable. One type of oral dosage form is the oral solution or suspension of glutathione. Oral solutions of reduced glutathione can be effectively delivered and absorbed in human subjects. Elevated plasma levels of glutathione can be realized through this form of administration. See Jones et al., *FASEB Journal*, vol. 3, p. A1250, 1990; "Glutathione Centennial: Molecular Perspectives and Clinical Implications", Academic Press, New York 1990, pp. 423-431.

While this represents a significant advantage over other forms of administration, oral suspensions of glutathione have disadvantages which render them much less desirable than solid oral dosage forms. Glutathione slurries have a foul, sulfurous taste which is thoroughly objectionable to a patient and difficult to mask. Furthermore, oral suspensions require fresh preparation because glutathione is unstable in aqueous solutions. This renders them inconvenient, and undesirable, particularly where long term compliance to a medical regimen by a patient is essential.

The desirability of solid dosage forms such as a tablets or capsules is therefore manifest. Unfortunately, glutathione is not very accommodating to such dosage forms.

Reduced L-glutathione has an unusually high electrostatic charge. As described in more detail herein, this renders the material difficult to encapsulate or tablet. This problem is greatly exacerbated during processing. For example, standard encapsulation equipment moves powder from a reservoir hopper into a dosing trough, then into a dosator funnel. From the dosator funnel, the powder material is emptied into empty capsules or tablet dies which are then sealed or pressed and cleaned in a cleaning/polishing machine. Thereafter, the filled cleaned capsules or tablets are moved to any of a number of different packaging devices. But much like a balloon rubbed against a sweater, glutathione picks up significant additional electrostatic charge during this processing. The glutathione material then sticks and accumulates to the processing machinery, wreaking havoc with its smooth and consistent operation.

Moreover, it is almost impossible to obtain complete and reliable fill weights in capsules or tablets. Overfilling and underfilling are common. Most frustratingly, however, is the problem of highly variable fill levels between batches and in fact, between individual capsules in a batch.

The problems with the processing of glutathione do not end there.

Once the capsules or tablets have been completed, they are cleaned and polished. This process often involves brushing, wiping and the like to remove residual powder from the exterior of the capsule. The movement of the capsules is rapid, with rotating brushes, or cloths buffing them. This combination adds an additional charge to the interior powder, as well as powder clinging to the inner and outer surfaces of capsules. Because of the high electrostatic forces generated during the prior processing steps, glutathione remains on the surface of the tablet or capsule. Moreover, the very process of attempting to remove excess glutathione from the exterior surface of the capsule merely increases the amount of electrostatic charge which results. The net of all the acquired and inherent charges becomes so great at this stage that visible sparking, three to four centimeters long, is routinely experienced when attempting to handle glutathione capsules or tablets having a fill weight of 250 mg of glutathione or more.

Other problems are exhibited when attempting to package high fill weight glutathione capsules and tablets. For example, when a vibrating hopper with inclined guide device is used to transport the now cleaned capsules to individual packages, the highly charged glutathione capsules or tablets tend to fall onto the incline guide and stick thereto. Even when vibration is applied to the inclined guide, to urge the solid dosage form onward, packages tend to be underfilled or overfilled more often than they are filled to the appropriate level.

Other types of packaging devices utilize oscillating gravity feeders. These feed devices lift the capsules or tablets up into small enclosed guide tracks that depend on gravity. However, this process adds additional charge and the highly charged capsules or tablets entering the opening of the guide tracks frequently would stop within the enclosed guides and jam.

To overcome these problems, a number of solutions have been suggested. First, it is possible to use relatively low amounts of glutathione. This will limit the amount and the effect of the electrostatic buildup. Unfortunately, experts believe that relatively high daily dosages of glutathione will be required to be effective in the treatment of the toxicities of adriamycin, cisplatin and cyclophosphamide toxicities, cardiovascular disorders and, immunologic disorders such as acquired immune deficiency syndrome ("AIDS"). To attain such daily dosage levels with low fill weight glutathione solid dosage forms, literally dozens of capsules would have to be consumed on a daily basis. Long term compliance by a patient to such an unwieldy dosage regimen is difficult. This is particularly true in the case of persons who find it difficult to take tablets or capsules in the first place.

It is also possible to mix small amounts of glutathione, below 100 mg with, for example, an overwhelming amount of lubricants, excipients, fillers, binders or other adjuvants. Again, however, accommodating high daily dosages will require the daily administration of possibly dozens of tablets or capsules a day. In addition, to accommodate the various adjuvants, the size of the tablet or capsule may need to be increased, making it more difficult for patients to swallow and exacerbating the problems encountered with administration to people who are idiosyncratic about swallowing tablets or capsules. In addition, the prolonged ingestion of excipient or additive rich capsules or tablets in the quantities necessary to administer sufficient glutathione on a daily basis is less than desirable. Adverse reactions to excipients and additives include: 1) serious gastrointestinal reactions, such as nausea, vomiting, cramps, bloating, diarrhea and persistent flatulence; 2) skin rashes; 3) dizziness, tinnitus; 4) hypotension.

Such an administration scheme represents almost the worst of all possible worlds.

The present inventors attempted a number of possible solutions with regard to high glutathione level capsules and tablets. First, the present inventors attempted the use of small and large amounts of magnesium stearate, calcium carbonate, talc, silicon dioxide, starches and/or dry powdered ascorbic acid. Rather than dissipating the electrostatic charge, some of these agents actually increased the problem. The inventors also attempted to generate a flow of ions, positively and negatively charged, directed at the capsules and the powder. These techniques did not, however, prove satisfactory in the reliable production of large numbers of high fill weight glutathione capsules or tablets.

The problems associated with the production of glutathione tablets are further complicated by the relatively low bulk density and poor compressibility of reduced L-glutathione.

The present inventors have, however, discovered a solution to the problems associated with the production of high glutathione content capsules and tablets.

OBJECTS AND SUMMARY OF THE INVENTION

One object of the present invention is the provision of a method for alleviating, neutralizing, or otherwise dissipating the electrostatic forces found in glutathione as well as those which are generated in forming solid dosage forms therefrom.

It is another object of the present invention to provide for methods of controlling the electrostatic charge of glutathione so as to render it capable of being tableted or encapsulated without the need for the use of objectionable adjuvants.

In accordance with this aspect of the present invention, there is provided a method of dissipating the electrostatic charge of glutathione so as to render it capable of being formed into a high glutathione content solid dosage form including the steps of: providing glutathione, providing crystalline ascorbic acid in an amount effective to dissipate the electrostatic charge of the glutathione, and mixing the glutathione and the crystalline ascorbic acid for a time sufficient to dissipate the electrostatic charge of the glutathione.

It has been discovered, quite unexpectedly, that the addition of a relatively small amount of a specific crystalline form of ascorbic acid can alleviate, neutralize, or otherwise dissipate the electrostatic charge problems attendant the handling of reduced L-glutathione and, in particular, the formation of tablets and capsules therefrom. This finding is particularly surprising in light of the fact that the use of conventional dried powder ascorbic acid does nothing to dissipate the electrostatic charge of glutathione and in fact, can exacerbate the problems associated with the formation of solid dosage forms therefrom.

It is an object of the present invention to provide oral dosage forms of glutathione which will promote patient compliance with long term, high daily dosage level administration protocols.

It is also an object of the present invention to provide glutathione in solid dosage form having a relatively high content of glutathione without the inclusion of objectionable levels of adjuvants or the incorporation of otherwise objectionable adjuvants.

In accordance with these objectives, one aspect of the present invention is the provision of an oral dosage form consisting essentially of glutathione and an amount of crystalline ascorbic acid effective to neutralize the electrostatic charge of said glutathione.

Preferably, the amount of crystalline ascorbic acid present in oral dosage forms in accordance with the present invention is at least one milligram per 10 milligrams of glutathione and more preferably between about 1 milligram and about 4 milligrams per 10 milligrams of glutathione. Glutathione dosage forms including at least 250 mg of glutathione may be produced in accordance with the present invention in a convenient size and shape such as a single 0 capsule.

This provides for relatively high dosage levels of glutathione, without the need for the ingestion of a large number of tablets or capsules on a daily basis and/or without the need to resort to objectionably sized solid oral dosage forms. More preferably, glutathione may be provided in an amount of between about 250 and 750 mg in conventionally sized tablets and capsules ranging from single 0 to double 0 capsules. Most preferably, about 500 mg of glutathione and about 125 mg of crystalline ascorbic acid are used to formulate oral dosage forms in accordance with the present invention.

It is also possible to provide a buffering agent such as calcium carbonate, U.S.P. grade, precipitated, in accordance with the present invention to offset any intestinal discomfort that the ascorbic acid might cause.

DETAILED DESCRIPTION OF THE PREFERRED EMBODIMENTS

Crystalline ascorbic acid in accordance with the present invention is described in Demopoulos, U.S. Pat. No. 4,454,125, the text of which is hereby incorporated by reference and may be obtained Calcium carbonate, U.S.P. grade, precipitated, if included in the formulations in accordance with the present invention, can come from any number of commercial sources including Whittaker, Clark, and Daniels, Inc. According to the Merck Index, 9th Edition, calcium carbonate exists in nature in the minerals argonite, calcite and vaterite. Calcium carbonate is generally an odorless, tasteless powder or crystal which is practically insoluble in water.

Glutathione in accordance with the present invention refers to the reduced form of L-glutathione as a monomer. Glutathione in pure form is commercially available from a number of sources such as Kyowa Hakko Kogyo Co. Ltd., Tokyo, Japan, Kohjin Co. Ltd., Tokyo Japan and Recordati, Inc., Milan, Italy, and may be obtained naturally from yeast or synthetically See, for example, U.S. Pat. No. 3,281,407, the text of which is hereby incorporated by reference.

In the formulations in accordance with the present invention, it is important that sufficient crystalline ascorbic acid be provided with relation to the amount of glutathione to be delivered. The amount of crystalline ascorbic acid should be sufficient to effectively neutralize the electrostatic properties of the reduced glutathione and to render the reduced glutathione susceptible to convenient tableting or encapsulation.

The ratio of crystalline ascorbic acid to glutathione should preferably be at least about 1 mg per 10 mg of reduced glutathione. More preferably, the amount of crystalline ascorbic acid utilized should be between about 1 mg and about 4 mg of crystalline ascorbic acid per 10 mg of glutathione. Most preferably, about 2.5 mg of crystalline ascorbic acid per 10 mg of reduced glutathione is used.

In terms of, for example, a 500 mg tablet or capsule, the amount of crystalline ascorbic acid provided should range from between about 50 to about 200 mg and, most preferably, about 125 mg.

The amount of glutathione which may be provided in tablets or capsules in accordance with the prese invention ranges from between about 250 to about 750 mg in single 0 to double 0 sized capsules, with equivalent dimensions for tablets. Depending upon the specific conditions and the apparatus used, it may not be necessary to use as much crystalline ascorbic acid per unit glutathione as would result under other encapsulating or tableting conditions. Under these specific conditions, there may be room in tablets or capsules of the size previously described to incorporate up to 1000 mg of glutathione. It is also possible to manufacture tablets or capsules having, for example, 1000 mg of glutathione, even with higher levels of crystalline ascorbic acid. However, such formulations are somewhat less desirable as they necessarily encompass the use of larger tablets and capsules, a triple O capsule or equivalent dimensions for a tablet.

It is also possible to include calcium carbonate or other buffering agents such as calcium bicarbonate and calcium phosphate within the tablets or capsules of the present invention. These buffering agents do not appreciably exacerbate the electrostatic charge problems associated with glutathione and do assist in mitigating any potential objectionable side effects of the long term co-administration of relatively high levels of ascorbic acid. When present, these buffering agents are provided in an amount of between about 2 mg and about 10 mg per 10 mg of ascorbic acid and, more preferably, about 5 mg per 10 mg of ascorbic acid.

It may be possible to add other adjuvants to the solid dosage forms of the present invention. However, certain adjuvants may exacerbate the electrostatic charge phenomena observed in reduced glutathione Of course, it is preferred that such adjuvants not be used at all. But where such adjuvants are used, it is essential that they be used in relatively small amounts, totalling no more than about 5%. Other adjuvants which will not increase the electrostatic charge problems of glutathione can be used somewhat more liberally. However, the amounts of additional adjuvants should not be sufficient so as to pose a potential health problem when the resulting dosage forms are taken as part of a high glutathione content daily dosage regime. Most preferably, no other adjuvants including excipients, lubricants, tableting aids, binders or fillers are utilized in accordance with the present invention.

The present invention also provides for a method of eliminating, neutralizing, or otherwise dissipating the electrostatic charge associated with glutathione and its formulation into solid dosage forms. The methods involve providing a sufficient amount of crystalline ascorbic acid to dissipate the electrostatic charge of glutathione and mixing the glutathione and the crystalline ascorbic acid together for a time which is sufficient to dissipate the glutathione's electrostatic charge. Once the electrostatic charge has been dissipated, subsequent manipulation of the glutathione ascorbic acid mixture does not, apparently, result in the disadvantages which otherwise plague the tableting or encapsulation of glutathione.

In order to dissipate the charge inherent in glutathione in addition to the charge generated during processing, it is necessary to mix the crystalline ascorbic acid and glutathione for a minimum of 10 minutes and a maximum of about 25 minutes. Prolonged mixing results in fracturing the ascorbic acid crystals and loss of its benefits in charge dissipation. The preferred ratio of 1 mg crystalline ascorbic acid to 4 mg of glutathione requires 17 minutes, optimally. As the proportion of crystalline ascorbic acid is reduced, the mixing time becomes longer, such that a 1:10, crystalline ascorbic acid:glutathione, will require 25 minutes of mixing. The buffering agents, such as calcium carbonate, can be added at any time. If the electrostatic charge has not been dissipated, because of insufficient crystalline ascorbic acid, or inadequate mixing time, the acquisition of additional charges due to processing will occur.

The foregoing will be better understood with reference to the following examples. These examples are for the purposes of illustration. They are not to be considered limiting as to the scope and nature of the present invention.

EXAMPLE 1

| Dissipation of Electrostatic Charge of Glutathione | |
|---|---|
| Formulation | Amount for 100,000 capsules, 500 mg each |
| A. Glutathione | 50.00 kg |
| B. Glutathione | 50.00 kg |
| Crystalline Ascorbic Acid | 12.50 kg |

Both A and B were mixed for 17 minutes in a Patterson-Kelly Twin-Shell blender, 10 ft$^3$ capacity.

The powder adhered to the side walls of this V-shaped blender during the processing of A and could not exit at the apex due to the "bridging" phenomenon caused by the intense adherence of the glutathione. The material had to be pushed away from the side walls with scraping devices, using the top access portals.

There was no adherence of any significance to the side walls of this V-shaped blender during the processing of B.

TABLE I

| | CHARGE DENSITY (VOLTAGE AT 1″ FROM POWDER) | |
|---|---|---|
| Glutathione source | Powder 1A Glutathione alone | Powder 1B Glutathione with Crystalline Ascorbic Acid |
| Tanabe GSH | 2000 volts | decrease of 400 volts (80%) |
| Kyowa Hakko GSH | 4000 volts | decrease of 900 volts (77.5%) |
| Ajinomoto GSH | 6000 volts | decrease of 950 volts (84.2%) |

The charge density of powders A and B were also measured. This was accomplished by conducting measurements after 10 minutes agitation with a Static Meter from Monroe Electronics, Inc., Lyndonville, N.Y., Stat-Arc II, Model 265. The results are reported in Table I.

EXAMPLE 2

A and B, from Example above, were encapsulated using an MG-America, type MG2, model G37/N continuous motion capsule filling machine The speed setting of the machine was 89,000 capsules/hour, using two-piece, hard, clear gelatin capsules, size 00. The capsules were weighed for their fill-weights. In the next step, the capsules were fed into the MG-America model GTS capsule cleaner after filling and then were loaded into the capsule reservoir of the Klockner Wolkogen Compacker blister packaging machine with brush feeder, model 8/EL, set at 45 cycles per minute.

A. The fill weights, 500 mg, were highly erratic:
288 mg
340 mg
420 mg
486 mg

The capsules were highly charged and emitted sparks of 3 to 4 cm length when they were moved for handling or transferring.

The capsules could not be fed reliably into the blister packaging machine. They would cling to the side walls of the reservoir.

B. The fill weights, 625 mg, were within an acceptable range:
612 mg
620 mg
630 mg
638 mg The capsules did not emit sparks when handled, or transferred.

The capsules fed reliably into the blister packaging machinery.

EXAMPLE 3

The combination of glutathione mixed with either powdered ascorbic acid or crystalline ascorbic acid were compared in terms of bulk powder densities and electrostatically charged adherence. Table II compares the powder bulk density of glutathione commercially obtained from there sources.

TABLE II

| Glutathione | Glutathione with Powdered Ascorbic Acid 2:1 mixture | Glutathione with Crystalline Ascorbic Acid 2:1 mixture |
|---|---|---|
| 16.67 lb/ft$^3$ Tanabe GSH | 19.24 lb/ft$^3$ (15%) | 25.01 lb/ft$^3$ (50%) increase |
| 19.24 lb/ft$^3$ Kyowa Hakko GSH | 21.93 lb/ft$^3$ (14%) | 27.79 lb/ft$^3$ (44%) increase |
| 14.71 lb/ft$^3$ Ajinomoto GSH | 16.18 lb/ft$^3$ (10%) | 19.24 lb/ft$^3$ (30%) increase |

*Carried out under standard room temperature & pressure, with 26% R.H.

The addition of powdered ascorbic acid to glutathione increased the bulk powder density between about 10 to about 15% over glutathione alone. The addition of crystalline ascorbic acid to glutathione increased the bulk powder density between about 30 to about 50% over glutathione alone. Crystalline ascorbic acid therefore produces glutathione powders which are dramatically heavier and easier to handle and tablet or encapsulate.

Electrostatic charge dissipation can be measured in terms of the degree of electrostatically charged adherence of the glutathione containing powder to the vertical walls of a stainless steel square.

Three grams of each powder was evenly dispersed onto a chemically clean stainless steel plate, 50.00 cm$^2$ surface area and allowed to sit for two minutes. A square, measuring 7.071 cm, per side, was washed off on a larger plate to provide the 50 cm$^2$ area, with adequate surrounding margins. The plate was then slowly raised to the vertical without jarring and the non-adhering material collected and weighed. The results are reported in Table III.

TABLE III

| Glutathione | Glutathione with Powdered Ascorbic Acid 2:1 mixture | Glutathione with Crystalline Ascorbic Acid 2:1 mixture |
|---|---|---|
| 22.65% of Powder adheres | 77.13% of Powder adheres | 0% of Powder adheres |

*Carried out under standard room temperature & pressure, with 26% R.H.

Almost 25% of the glutathione adhered to the steel surface without any form of ascorbic acid. This adherence is due to the inherent electrostatic charge of glutathione. When powdered ascorbic acid was added to glutathione, the percentage of adherence nearly tripled. Thus powdered ascorbic acid only serves to increase the electrostatic charge which plagues glutathione.

In contrast, a mixture of glutathione and crystalline ascorbic acid in the same ratio exhibits a 100% decrease in electrostatic charge when compared to glutathione alone and a 300% decrease in electrostatic charge when compared to a mixture of glutathione and powder ascorbic acid.

This result was unexpected because while both forms of ascorbic acid provided some level of increase in bulk powder density, diametrically opposed results were observed in terms of electrostatic charge dissipation.

EXAMPLE 4

Reduced L-glutathione was converted into capsules using an MG America, Type MG-2, model G37/N encapsulation device. The device included a rotating circular dosing trough, dosator funnels, capsule staging and assembling mechanisms and capsule cleaning and polishing machines.

It was observed that the rotating circular dosating trough, by itself, imparts a high acquired charge to glutathione alone. This resulted in irregular levels of powder of different densities in the trough. Not only did this impede the proper functioning of the dosator trough, but this problem contributed to erratic filling of the dosator funnels and, subsequently, the capsules.

This particular type of encapsulation device includes a sensor, termed a "float", which rides on the surface of the powder which is circling around in the rotating dosating trough. The sensor relies on magnetoelectrical impulses which signals the reservoir to release more raw glutathione into the dosating trough. Because of the problems associated with the electrostatic activity of glutathione, and its low bulk density, the float malfunctioned completely. This produced erratic releases of material into the dosator, further complicating the dosator trough operation and the level of predictable fill for capsules.

The filling of capsules is completely erratic from the dosating funnels because of the variable levels of powder released and because of the propensity for the material to stick to the sides of the dosating trough, dosating funnel, and other equipment. Dosators routinely jammed and powder loss became significant. Glutathione is expensive enough without being inadvertently released out of the encapsulating system.

Similar problems were observed during the use a Zanasi AZ-20 encapsulation device. The Zanasi machine does not include a float sensor so no similar problem was observed in its use.

EXAMPLE 5

A semi-automated encapsulation device, Parke-Davis Type 8, was utilized where the movement of powder is facilitated by a conical powder hopper that contains a rotating auger. The acquired charge from this movement precluded reproducible dosing and filling of the capsules and unacceptable quantities of glutathione were released. The capsule fill weights, which were supposed to be 500 mg, were 216 mg, 339 mg, 384 mg, 409 mg in double O capsules.

It is apparent that the encapsulation of glutathione alone is difficult. These difficulties are not overcome by the use of, for example, traditional dry powder forms of ascorbic acid. Only by the practice of the present invention are acceptable results obtained. The principles, preferred embodiments, and modes of operation of the present invention have been described in the foregoing specification. The invention which is intended to be protected herein, however, is not to be construed as limited to the particular embodiments disclosed, since these are to be regarded illustrative rather than restrictive. Variations and changes may be made by others without departing from the spirit and scope of the invention.

We claim:

1. An oral dosage form consisting essentially of glutathione and an amount of crystalline ascorbic acid effective to neutralize the electrostatic charge of said glutathione.

2. The oral dosage form of claim 1 wherein said crystalline ascorbic acid is present in an amount of at least about 1 mg per 10 mg of said glutathione.

3. The oral dosage form of claim 2 wherein said crystalline ascorbic acid is present in an amount of between about 1 mg and about 4 mg per 10 mg of said glutathione.

4. The oral dosage form of claim 3 wherein said crystalline ascorbic acid is present in an amount of about 2.5 mg per 10 mg of said glutathione.

5. The oral dosage form of claim wherein said glutathione is present in an amount of at least about 250 mg.

6. The oral dosage form of claim 5 wherein lutathione is present in an amount of between about 250 mg and about 750 mg.

7. The oral dosage form of claim 6 wherein said glutathione is present in an amount of about 500 mg.

8. An oral dosage form consisting essentially of glutathione and an amount of crystalline ascorbic acid effective to neutralize the electrostatic charge of said glutathione and an amount of buffering agent effective to buffer the effects of said crystalline ascorbic acid on the digestive tract of a human.

9. The oral dosage form of claim 8 wherein said buffering agent is selected from the groups consisting of calcium carbonate, calcium bicarbonate and calcium phosphate.

10. The oral dosage form of claim 9 wherein said buffering agent is calcium carbonate.

11. The oral dosage form of claim 8 wherein said buffering agent is present in a amount of at least about 2 mg per 10 mg ascorbic acid.

12. The oral dosage form of claim 11 wherein said buffering agent is present in an amount of between about 2 mg and about 10 mg per 10 mg of ascorbic acid.

13. The oral dosage form of claim 12 wherein said buffering agent is present in an amount of about 5 mg per 10 mg of ascorbic acid.

14. A method of dissipating the electrostatic charge of glutathione so as to render it capable of being formed into a high glutathione content solid dosage form comprising the steps of:
   providing glutathione;
   providing crystalline ascorbic acid in a amount effective to dissipate the electrostatic charge of said glutathione; and
   mixing said glutathione and said crystalline ascorbic acid for a time sufficient to dissipate said electrostatic charge of said glutathione.

15. The method of claim 14 wherein said crystalline ascorbic acid is provided in an amount of at least about 1 mg per 10 mg of said glutathione.

16. The method of claim 15 wherein said crystalline ascorbic acid is provided in an amount of between about 1 mg and about 4 mg per 10 mg of said glutathione.

17. The method of claim 16 wherein said crystalline ascorbic acid is provided in an amount of about 2.5 mg per 10 mg of said glutathione.

18. The method of claim 16 wherein said time sufficient to dissipate said electrostatic charge ranges from between about 10 and about 25 minutes.

19. The method of claim 17 further comprising the step of tableting said mixture of glutathione and crystalline ascorbic acid.

20. The method of claim 17 further comprising the step of encapsulating said mixture of glutathione and crystalline ascorbic acid.

* * * * *

UNITED STATES PATENT AND TRADEMARK OFFICE
CERTIFICATE OF CORRECTION

PATENT NO. : 5,204,114
DATED     : April 20, 1993
INVENTOR(S) : Demopoulos et al.

It is certified that error appears in the above-indentified patent and that said Letters Patent is hereby corrected as shown below:

Column 1, line 32, "ha" should read --has--.
Column 2, line 15, "frustratingly" should read --frustrating--.
Column 4, line 61, after the word "obtained", please insert --.--.
Column 5, line 33, "prese" should read --preset--.
Column 5, line 65, after the word "glutathione", please insert --.--.
Column 7, line 22, after the word "Example", please insert --1--.
Column 7, line 61, "there" should read --three--.
Column 8, line 25, "was" should read --were--.
Column 10, line 10, "lutathione" should read --said glutathione--.

Signed and Sealed this

Twenty-fifth Day of January, 1994

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO.   : 5,204,114
DATED        : April 20, 1993
INVENTOR(S)  : Demopoulos et al.

Page 1 of 1

It is certified that error appears in the above-identified patent and that said Letters Patent is hereby corrected as shown below:

Column 10,
Line 8, "5. The oral dosage form of claim wherein said" should read
-- 5. The oral dosage form of claim 1 wherein said --

Signed and Sealed this

Eleventh Day of March, 2003

JAMES E. ROGAN
*Director of the United States Patent and Trademark Office*